United States Patent [19]

Eschenmoser et al.

[11] 4,328,383

[45] May 4, 1982

[54] PROCESS FOR PREPARING UNSATURATED BICYCLIC HYDROCARBONS

[75] Inventors: Albert Eschenmoser, Küsnacht; Dorothee Felix, Zürich, both of Switzerland

[73] Assignee: S. A. Firmenich, Geneva, Switzerland

[21] Appl. No.: 224,193

[22] Filed: Jan. 12, 1981

[30] Foreign Application Priority Data

Jan. 18, 1980 [CH] Switzerland .......................... 398/80

[51] Int. Cl.$^3$ .............................................. C07C 1/20
[52] U.S. Cl. .................................................. 585/357
[58] Field of Search ........................................ 585/357

[56] References Cited

PUBLICATIONS

Eschenmoser Chem. Abst. 70 (1969) #88108.
Nair et al., J. Chem. Soc. 1964, pp. 4154–4157.
Mamdapur et al., Tet. 20(1964) pp. 2601–2604.

*Primary Examiner*—Arthur P. Demers
*Attorney, Agent, or Firm*—Scully, Scott, Murphy & Presser

[57] ABSTRACT

New process for preparing unsaturated bicyclic hydrocarbons useful as intermediate compounds in the preparation of macrocyclic ketones.

4 Claims, No Drawings

NEW PROCESS FOR PREPARING UNSATURATED BICYCLIC HYDROCARBONS

SUMMARY OF THE INVENTION

The invention relates to a process for preparing an unsaturated bicyclic hydrocarbon having the formula

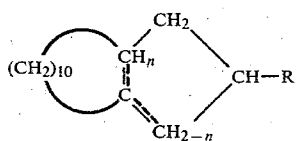

possessing a double bond in one of the positions indicated by the dotted lines and wherein the index n is equal to zero or 1 and R represents a hydrogen atom or a methyl radical, which comprises reacting a compound having the formula

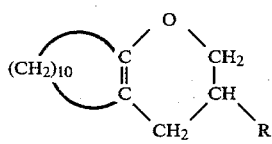

wherein symbol R is defined hereinabove with a triarylphosphine in the presence of a metal halide and optionally treating the thus obtained product with an isomerizing agent.

BACKGROUND OF THE INVENTION

EXALTONE ® and muscone, two macrocyclic ketones, are very appreciated in the art for their elegant and tenacious musky odour. Both compounds have been known for several decades and since their discovery a variety of syntheses have been proposed and described in the scientific literature [see: e.g. J. Chem. Soc. 1964, 4154; Tetrahedron 20, 2601 (1964); Helv. Chim. Acta 50, 705 (1967) and Helv. Chim. Acta 50, 708 (1967)]. So far, however, most of the published methods could not be successfully applied to their industrial scale preparation, especially in view of their complexity or in view of the low yields achieved in the critical reaction steps.

One of the prior known syntheses [Helv. Chim. Acta 50, 705 (1967)] is making use of the compound of formula

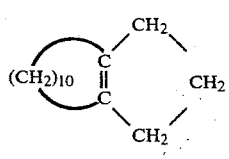

(R=H; n=zero in formula I) as intermediate in the synthesis of EXALTONE ® (cyclopentadecanone), and of the corresponding methyl derivative of formula

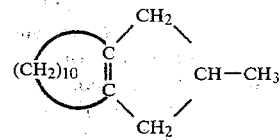

(R=methyl; n=zero in formula I) in the synthesis of muscone. Both intermediate compounds can be obtained from cyclododecanone, by a condensation reaction and a subsequent cyclization, hydrogenation and dehydration. Due to rather poor overall yields, however, such synthetic routes do not present any major interest to the industry.

The merit of the invention consists in proposing a new and original synthetic process for preparing the above mentioned intermediate compounds, by making use of cheap and easily available starting materials, viz. the bicyclic compounds of formula (II): 13-oxa-bicyclo[10.4.0]hexadec-1(12)-ene e.g. (R=H in formula II) is also used as starting material for preparing EXALTOLIDE ® [see in this respect DE-PS No. 2,026,056 and DE-AS No. 2,065,551].

PREFERRED EMBODIMENTS OF THE INVENTION

According to the invention, unsaturated bicyclic hydrocarbons of formula (I) are prepared from the compounds of formula (II) after treatment thereof by means of a triaryl-phosphine, preferably triphenyl-phosphine, in the presence of a metal halide. As metal halide one can advantageously use a lithium, magnesium, aluminum or zinc halide. Lithium bromide, chloride or iodide are preferably used, in proportions comprised between about 0.1 and 10%, more particularly between about 1 and 10% of the weight of starting compound of formula (II).

The said treatment is effected in the absence of additional solvent, at a temperature superior or equal to 250 degrees centigrade. The said treatment is preferably effected at a temperature of the order of 300 degrees centigrade and under an inert atmosphere, in a glass or steel autoclave, in this latter case preferably in a stainless steel autoclave fitted with internal glass walls. The reaction period mainly depends on the applied temperature: at about 300 degrees centigrade, one observes total disappearance of the reacting starting material of formula (II) within about 15 to 20 hours.

In most cases, the unsaturated bicyclic hydrocarbons of formula (I) thus prepared are obtained in the form of isomeric mixtures containing 90% or more of the isomer having a tetrasubstituted double bond as illustrated hereinafter;

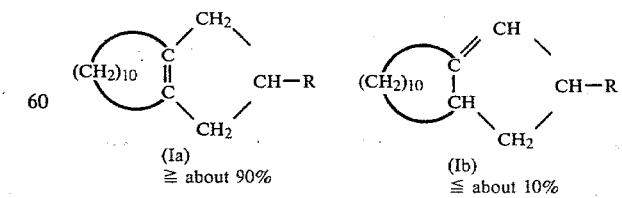

R = H or methyl

If requested, both isomers can be separately isolated from the obtained mixtures by means of conventional techniques, vapour phase chromatography e.g.

According to the invention, the obtained isomeric mixtures can alternatively be treated with an isomerizing agent, for instance a strong acid such as p-toluenesulfonic or benzenesulfonic acid, or even iodine. Isomer (Ia) is thus quantitatively isolated.

The following examples will illustrate the invention in a more detailed manner. In said examples, the temperatures are given in degrees centigrade and the abbreviations have the meaning common in the art.

EXAMPLE 1

Preparation of bicyclo[10.3.0]pentadec-1(12)-ene and bicyclo[10.3.0]pentadec-12-ene 10.0 g (45 mmole) of 13-oxa-bicyclo[10.4.0]hexadec-1(12)-ene and 12.3 g (47 mmole) of triphenyl-phosphine were heated 15 h at 300° in a stainless steel autoclave, under argon atmosphere, in the presence of 0.5 g of anhydrous lithium iodide. After cooling, the reaction mixture was diluted with chloroform, then subjected to fractional distillation to afford 7.7 g (85% yield) of a 10:1 mixture of bicyclo[10.3.0]pentadec-1(12)ene (compound A) and bicyclo[10.3.0]pentadec-12-ene (compound B) according to the vapour phase chromatography analysis, b.p. 90°/0.1 Torr.

The above reaction was repeated under different conditions as summarized hereinafter. In the table the proportions of lithium halide are given for 2 g of starting 13-oxa-bicyclo[10.4.0]hexadec-1(12)-ene.

| Lithium halide | Amounts (g) | Temp. (°) | Reaction time (h) | Yield (%) | A/B | Autoclave |
|---|---|---|---|---|---|---|
| LiBr | 0.1 | 300 | 16 | 70 | 10:1 | steel* |
| LiBr | 0.1 | 300 | 16 | 75 | 10:1 | glass |
| LiCl | 0.1 | 300 | 15 | 10 | — | steel* |
| LiCl | 0.2 | 300 | 48 | 65 | 8:1 | glass |
| LiI | 0.1 | 250 | 48 | 70 | 10:1 | steel* |

*stainless steel

Compounds A and B above were isolated in their pure state after separation by means of vapour phase chromatography (CARBOWAX 20 M 20% on silicagel—200°).

Bicyclo[10.3.0]pentadec-1(12)-ene (A)

NMR: 1.3 (18 H, m); 2.2 (8 H, m) δ ppm;
MS: m/e=206 (67), 135 (22), 121 (31), 94 (52), 82 (75), 81 (63), 80 (100), 67 (57), 55 (33), 41 (54).
$n_D^{23} = 1.5062$ Bicyclo[10.3.0]pentadec-12-ene (B)

NMR: 1.3 (20 H, m); 2.2 (4 H, m); 2.7 (1 H, m); 5.4 (1 H, m) δ ppm;
IR: 1650, 835 cm$^{-1}$.
$n_D^{23} = 1.5078$ The above identified compounds were found identical with a pure sample prepared according to known methods [J. Amer. Chem. Soc. 79, 5558 (1957)].

Pure bicyclo[10.3.0]pentadec-1(12)ene (A) was also prepared as follows: 5.95 g of the above 10:1 mixture of compounds A and B in solution in 85 ml of toluene, were heated to reflux for 4 h ½ in the presence of 530 mg of p-toluenesulfonic acid. After cooling, dilution with hexane, washing with an aqueous solution of sodium hydrogen carbonate and subsequently with sodium chloride in water, drying over magnesium sulfate, evaporation and distillation, there were isolated 5.41 g (91% yield) of the desired compound, b.p. 90° /0.1 Torr.

EXAMPLE 2

Preparation of 14-methyl-bicyclo[10.3.0]pentadec-1(12)-ene and 14methyl-bicyclo[10.3.0]pentadec-12-ene 10.0 g (42.5 mmole) of 15-methyl-13-oxa-bicyclo[10.4.0]hexadec-1(12)-ene and 12.3 g (47 mmole) of triphenyl-phosphine were heated 15 h at 300° in a glass autoclave, under argon atmosphere, in the presence of 0.25 g of anhydrous lithium iodide. After cooling the reaction mixture was diluted with chloroform and finally evaporated to afford 7.86 g of crude residue. After purification by means of column chromatography (silicagel -eluent: hexane) there were isolated 5.8 g (63% yield) of a 12:1 mixture of 14-methyl-bicyclo[10.3.0]pentadec-1(12)-ene (compound C) and 14-methyl-bicyclo[10.3.0]pentadec-12-ene (compound D) according to the vapour phase chromatography analysis.

The above reaction was repeated under different conditions as summarized hereinafter. In the following table the proportions of lithium halide are given for 2 g of starting 15-methyl-13-oxa-bicyclo[10.4.0]hexadec-1(12)-ene.

| Lithium halide | Amounts (g) | Temp. (°) | Reaction time (h) | Yield (%) | C/D | Autoclave |
|---|---|---|---|---|---|---|
| LiI | 0.05 | 300 | 17 | 57 | 12:1 | glass |
| LiBr | 0.04 | 300 | 17 | 51 | 9:1 | glass |
| LiBr | 0.1 | 300 | 17 | 43 | 9:1 | glass |
| LiCl | 0.2 | 300 | 48 | 10 | — | glass |
| LiI | 0.1 | 250 | 22 | 20 | 10:1 | glass |
| LiI | 0.1 | 250 | 48 | 47 | 10:1 | glass |
| LiBr | 0.1 | 250 | 48 | 10 | — | glass |

14-Methyl-bicyclo[10.3.0]pentadec-1(12)-ene (C)

b.p. 100°-110° /0.01 Torr
NMR: 1.0 (3 H, d, J=6 Hz); 1.3 (17 H, m); 2.2 (8 H, m) δ ppm;
MS: m/e=220 (100), 205 (6), 163 (8), 149 (20), 135 (29), 121 (26), 107 (66), 94 (98), 93 (79), 81 (89), 67 (52), 55 (67), 41 (77).

The above identified compound was found identical with a sample prepared according to Chem. Abstr. 70, 88108 v (1970).

14-Methyl-bicyclo[10.3.0]pentadec-12-ene (D)

b.p. 78°-85° /0.02 Torr
IR: 1650, 855 cm$^{-1}$;
NMR: 1.0 (1.5 H, d, J=6 Hz); 1.1 (1.5 H, d, J=6 Hz); 1.4 (18 H, m); 2.1 (2 H, m); 2.7 (2 H, m); 5.3 (1 H, m) δ ppm;
MS: m/e=220 (38), 205 (8), 135 (10), 107 (45), 94 (100), 93 (53), 81 (35), 67 (20), 55 (21), 41 (27).
$n_D^{23} = 1.5042$.

Pure 14-methyl-bicyclo[10.3.0]pentadec-1(12)-ene (C) was also prepared as follows: 0.53 g of the above 10:1 mixture of compounds C and D were heated during 4 h ½ in the presence of 0.02 g of iodine, under argon atmosphere. After distillation of the reaction mixture (b.p. 100°-110° /0.01 Torr) there were isolated 0.48 g (92% yield) of the desired compound.

What we claim is:
1. Process for preparing an unsaturated bicyclic hydrocarbon having the formula

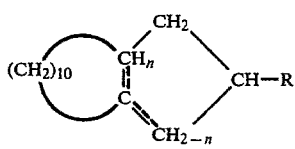
(I)

possessing a double bond in one of the positions indicated by the dotted lines and wherein the index n is equal to zero or 1 and R represents a hydrogen atom or a methyl radical, which comprises reacting a compound having the formula

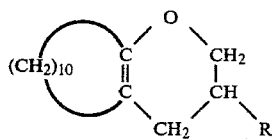
(II)

wherein symbol R is defined hereinabove with a triarylphosphine in the presence of a metal halide and optionally treating the thus obtained product with an isomerizing agent.

2. Process according to claim 1, which comprises using lithium, magnesium, aluminium or zinc halide as metal halide.

3. Process according to claim 1, which comprises treating the compound of formula (II) by means of triphenyl-phosphine in the presence of lithium halide.

4. Process according to claim 1, which comprises treating the compound of formula (II) at a temperature superior or equal to about 250 degrees centigrade.

* * * * *